US010973515B2

(12) United States Patent
Harris et al.

(10) Patent No.: US 10,973,515 B2
(45) Date of Patent: Apr. 13, 2021

(54) PERMANENT ATTACHMENT MEANS FOR CURVED TIP OF COMPONENT OF SURGICAL STAPLING INSTRUMENT

(71) Applicant: Ethicon LLC, Guaynabo, PR (US)

(72) Inventors: Jason L. Harris, Lebanon, OH (US); Frederick E. Shelton, IV, Hillsboro, OH (US); Chester O. Baxter, III, Loveland, OH (US); Gregory J. Bakos, Mason, OH (US); Taylor W. Aronhalt, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 182 days.

(21) Appl. No.: 16/035,872

(22) Filed: Jul. 16, 2018

(65) Prior Publication Data

US 2020/0015815 A1    Jan. 16, 2020

(51) Int. Cl.
| | | |
|---|---|---|
| *A61B 17/072* | (2006.01) | |
| *A61B 17/28* | (2006.01) | |
| *A61B 17/29* | (2006.01) | |
| A61B 17/064 | (2006.01) | |

(52) U.S. Cl.
CPC .......... *A61B 17/072* (2013.01); *A61B 17/282* (2013.01); *A61B 17/2909* (2013.01); *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01)

(58) Field of Classification Search
CPC ................ A61B 17/072; A61B 17/282; A61B 2017/07221; A61B 2017/2926; A61B 2017/2945
USPC .................................................. 227/176.1, 19
See application file for complete search history.

(56) References Cited

U.S. PATENT DOCUMENTS

| | | |
|---|---|---|
| 4,805,823 A | 2/1989 | Rothfuss |
| 5,014,899 A | 5/1991 | Presty et al. |
| 5,415,334 A | 5/1995 | Williamson et al. |

(Continued)

FOREIGN PATENT DOCUMENTS

| | | |
|---|---|---|
| EP | 2 777 523 A1 | 9/2014 |
| EP | 2772202 | 9/2014 |

(Continued)

OTHER PUBLICATIONS

European Search Report dated Aug. 7, 2018 for Application No. 18157228.0, 8 pages.

(Continued)

*Primary Examiner* — Chelsea E Stinson
(74) *Attorney, Agent, or Firm* — Frost Brown Todd LLC

(57) ABSTRACT

A surgical instrument includes a body, a shaft, and an end effector that is operable to compress, staple, and cut tissue. The end effector includes a pair of jaws. One of the jaws has a deflectable placement tip attached thereto. The placement tip may be attached using a mechanical connection in some versions. Still in other versions the placement tip may be attached via an overmolding process. Where an overmolding process is used, a portion of the jaw can be configured with various connection features that improve the overmolding attachment success.

20 Claims, 15 Drawing Sheets

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitma et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,066,166 B2 | 11/2011 | Demmy et al. | |
| 8,136,711 B2 * | 3/2012 | Beardsley | A61B 17/07207 227/175.1 |
| 8,210,411 B2 | 7/2012 | Yates et al. | |
| 8,348,123 B2 | 1/2013 | Scirica et al. | |
| 8,403,195 B2 | 3/2013 | Beardsly et al. | |
| 8,403,196 B2 | 3/2013 | Beardsly et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,496,153 B2 | 7/2013 | Demmy et al. | |
| 8,561,870 B2 | 10/2013 | Baxter, III et al. | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,690,039 B2 | 4/2014 | Beardsly et al. | |
| 8,714,429 B2 | 5/2014 | Demmy | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,844,790 B2 | 9/2014 | Demmy et al. | |
| 9,016,546 B2 | 4/2015 | Demmy et al. | |
| 9,039,736 B2 | 5/2015 | Scirica et al. | |
| 9,186,142 B2 | 11/2015 | Fanelli et al. | |
| 9,301,759 B2 | 4/2016 | Spivey et al. | |
| 9,433,416 B2 | 9/2016 | Beardsy et al. | |
| 9,517,065 B2 | 12/2016 | Simms et al. | |
| 9,522,004 B2 | 12/2016 | Demmy | |
| 9,597,078 B2 | 3/2017 | Scirica et al. | |
| 9,622,746 B2 | 4/2017 | Simms et al. | |
| 9,713,470 B2 | 7/2017 | Scirica et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,913,642 B2 | 3/2018 | Leimbach et al. | |
| 9,936,968 B2 | 4/2018 | Demmy et al. | |
| 9,943,311 B2 | 4/2018 | Scirica et al. | |
| 10,080,564 B2 | 9/2018 | Beardsly et al. | |
| 10,166,023 B2 | 1/2019 | Vendely et al. | |
| 2004/0243151 A1 | 12/2004 | Demmy et al. | |
| 2005/0216055 A1 | 9/2005 | Scirica et al. | |
| 2008/0269793 A1 * | 10/2008 | Scirica | A61B 17/07207 606/190 |
| 2014/0166723 A1 | 6/2014 | Beardsly et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239043 A1 * | 8/2014 | Simms | A61B 17/07207 227/176.1 |
| 2014/0239044 A1 | 8/2014 | Hoffman | |
| 2015/0173752 A1 | 6/2015 | Demmy et al. | |
| 2015/0272575 A1 | 10/2015 | Leimbach et al. | |
| 2015/0282809 A1 | 10/2015 | Shelton, IV et al. | |
| 2016/0143659 A1 | 5/2016 | Glutz et al. | |
| 2016/0278774 A1 | 9/2016 | Shelton, IV et al. | |
| 2017/0014125 A1 | 1/2017 | Shelton, IV et al. | |
| 2017/0055981 A1 | 3/2017 | Vendely et al. | |
| 2017/0086823 A1 | 3/2017 | Leimbach et al. | |
| 2018/0235609 A1 * | 8/2018 | Harris | A61B 17/07207 |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2018/0325514 A1 | 11/2018 | Harris et al. | |
| 2018/0325515 A1 | 11/2018 | Harris et al. | |
| 2018/0325516 A1 | 11/2018 | Harris et al. | |
| 2019/0000481 A1 * | 1/2019 | Harris | A61B 17/0686 |
| 2019/0076143 A1 * | 3/2019 | Smith | A61B 34/37 |

FOREIGN PATENT DOCUMENTS

| | | |
|---|---|---|
| EP | 2 913 010 A2 | 9/2015 |
| WO | WO 2004/096057 | 11/2004 |
| WO | WO 2017/083129 | 5/2017 |
| WO | WO 2018/152044 A1 | 8/2018 |
| WO | WO 2018/152046 A1 | 8/2018 |

OTHER PUBLICATIONS

International Search Report and Written Opinion dated Apr. 19, 2018 for International Application No. PCT/US2018/017751, 17 pages.
U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
GLS Total TPe Solutions, "Overmolding Guide," GLS Corporation, 2004, 31 pgs., downloaded from: https://web.archive.org/web/20180619020146if_/http://www.polyone.com:80/files/resources/Overmold_Design_Guide.pdf on Oct. 8, 2019, XP055629772, 18 pgs.
European Search Report, Partial and Provisional Written Opinion dated Oct. 22, 2019 for Application No. EP 19186243.2, 11 pgs.
European Search Report, Extended, and Written Opinion dated Jan. 27, 2020 for Application No. EP 19186243.2, 11 pgs.
International Search Report and Written Opinion dated Dec. 5, 2019 for Application No. PCT/IB2019/056039, 17 pgs.

* cited by examiner

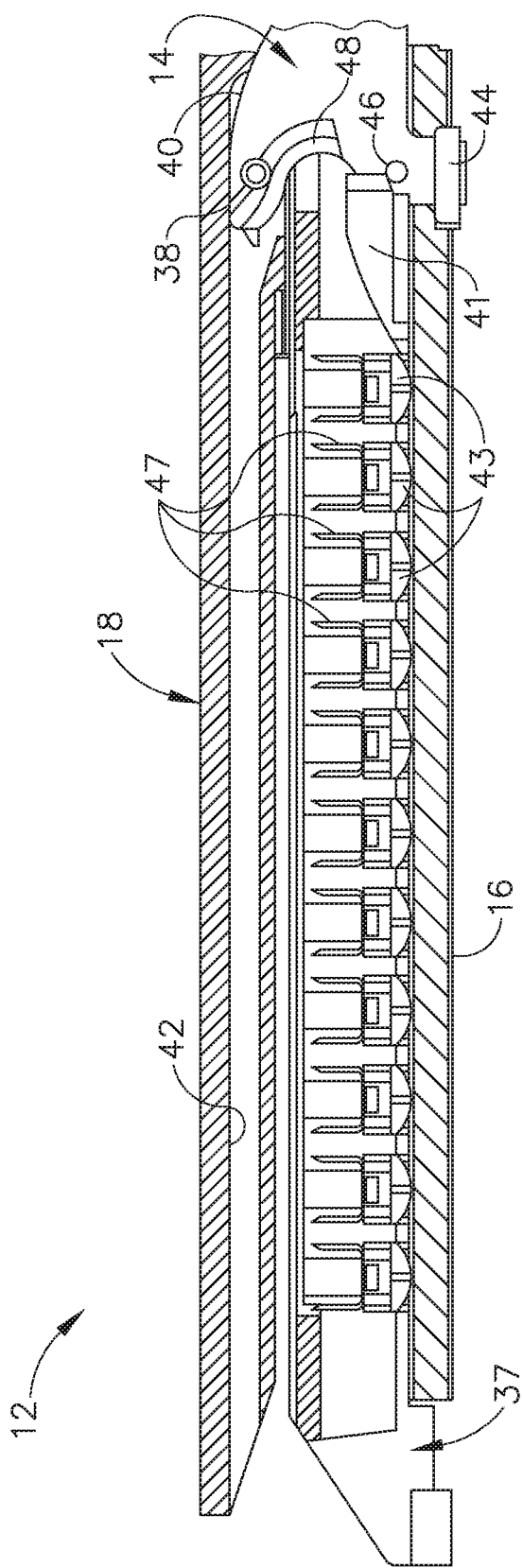

PERMANENT ATTACHMENT MEANS FOR CURVED TIP OF COMPONENT OF SURGICAL STAPLING INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with the firing beam in a proximal position;

Figure 1:
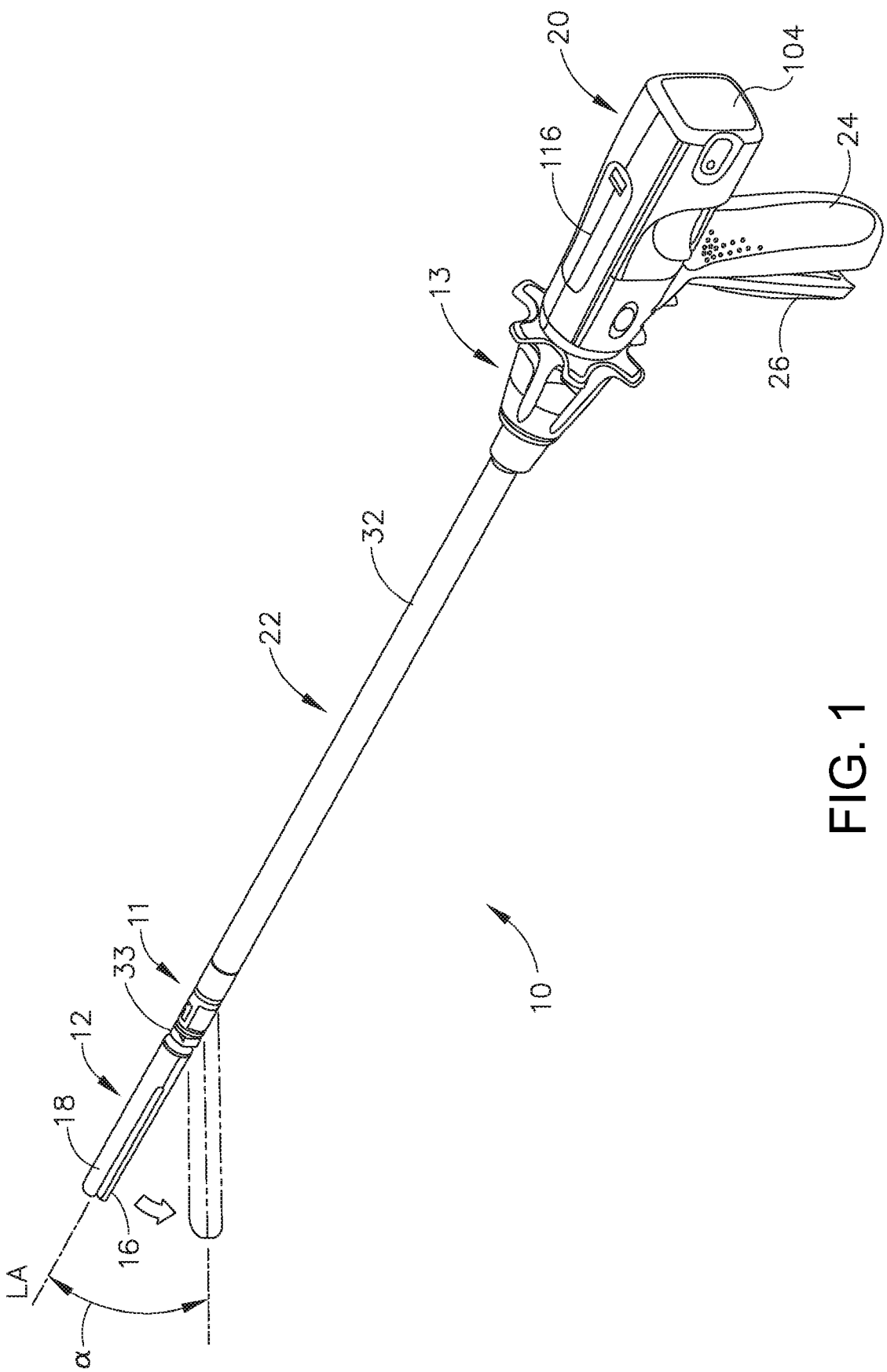
FIG. 1 depicts a perspective view of an exemplary articulating surgical stapling instrument.
Figure 2:
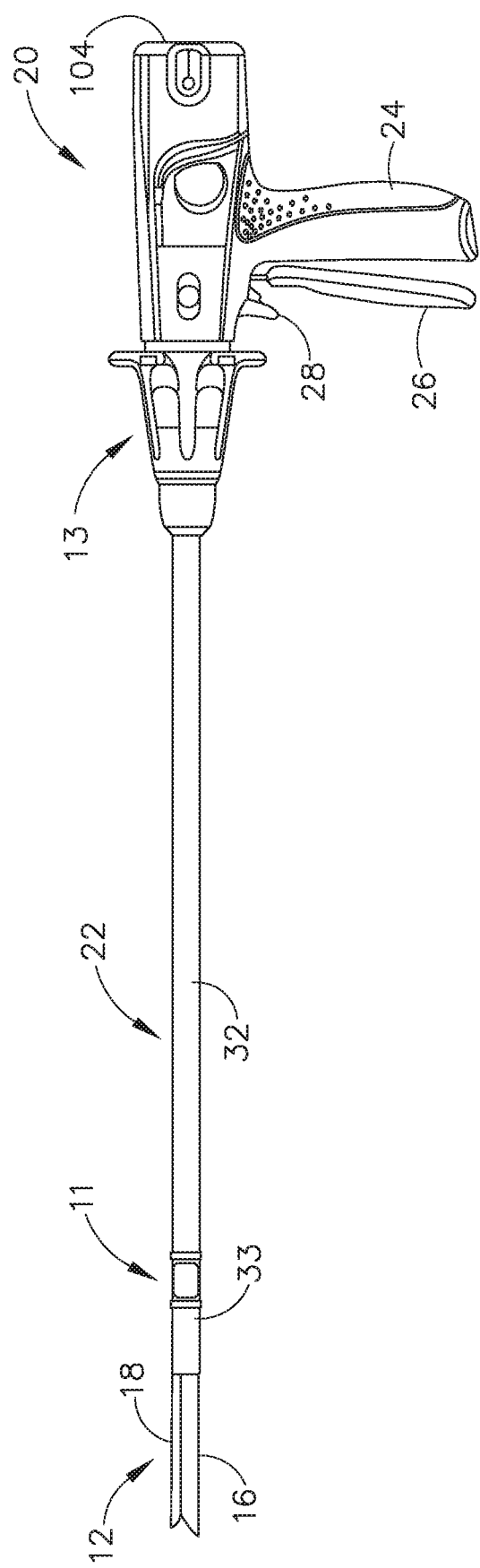
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In the present example, anvil (18) can also be considered an upper jaw. Furthermore, in some versions like the present example, the upper jaw or anvil (18) pivots with respect to a stationary lower jaw (16); however, in some other versions the upper jaw or anvil (18) is stationary while the lower jaw (16) pivots. In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092, 292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
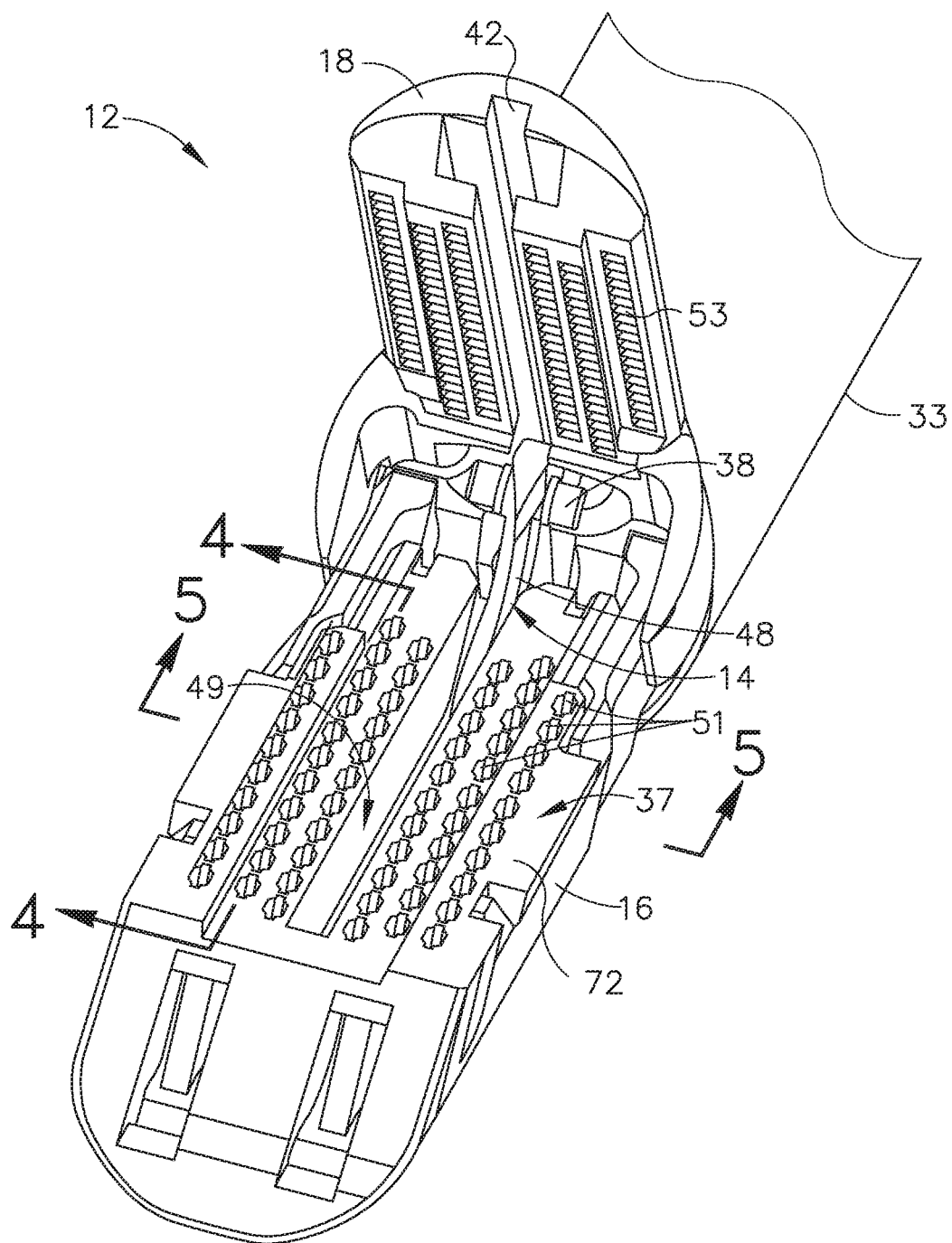
FIG. 3 depicts a perspective view of an opened end effector of the instrument of FIG. 1.
Figure 4B:
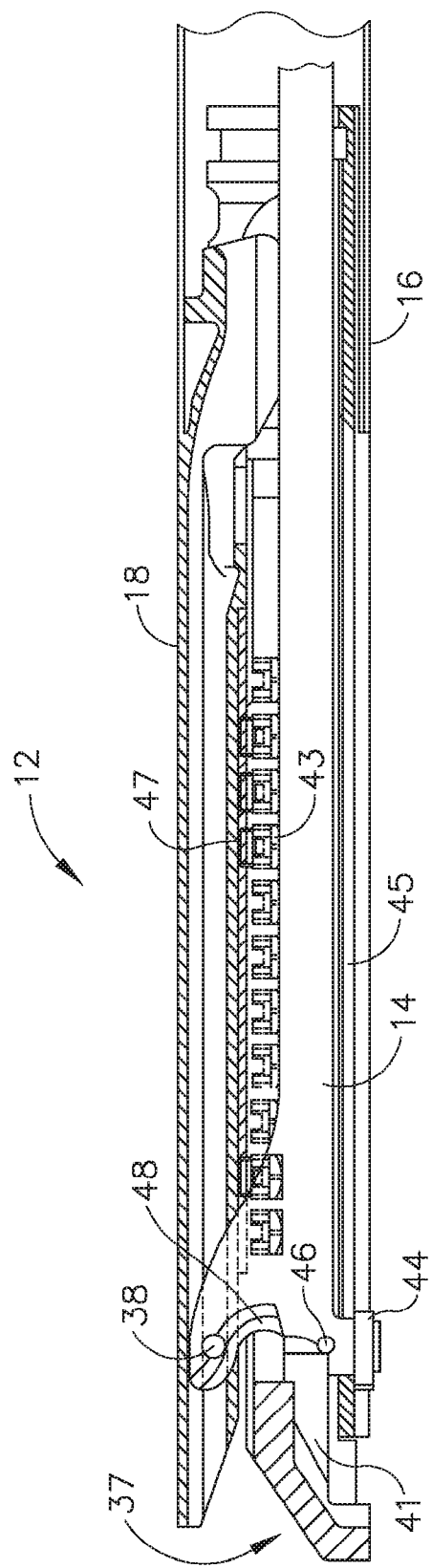
FIG. 4B depicts a side cross-sectional view of the end effector of FIG. 3, taken along line 4-4 of FIG. 3, with the firing beam in a distal position.
Figure 5:
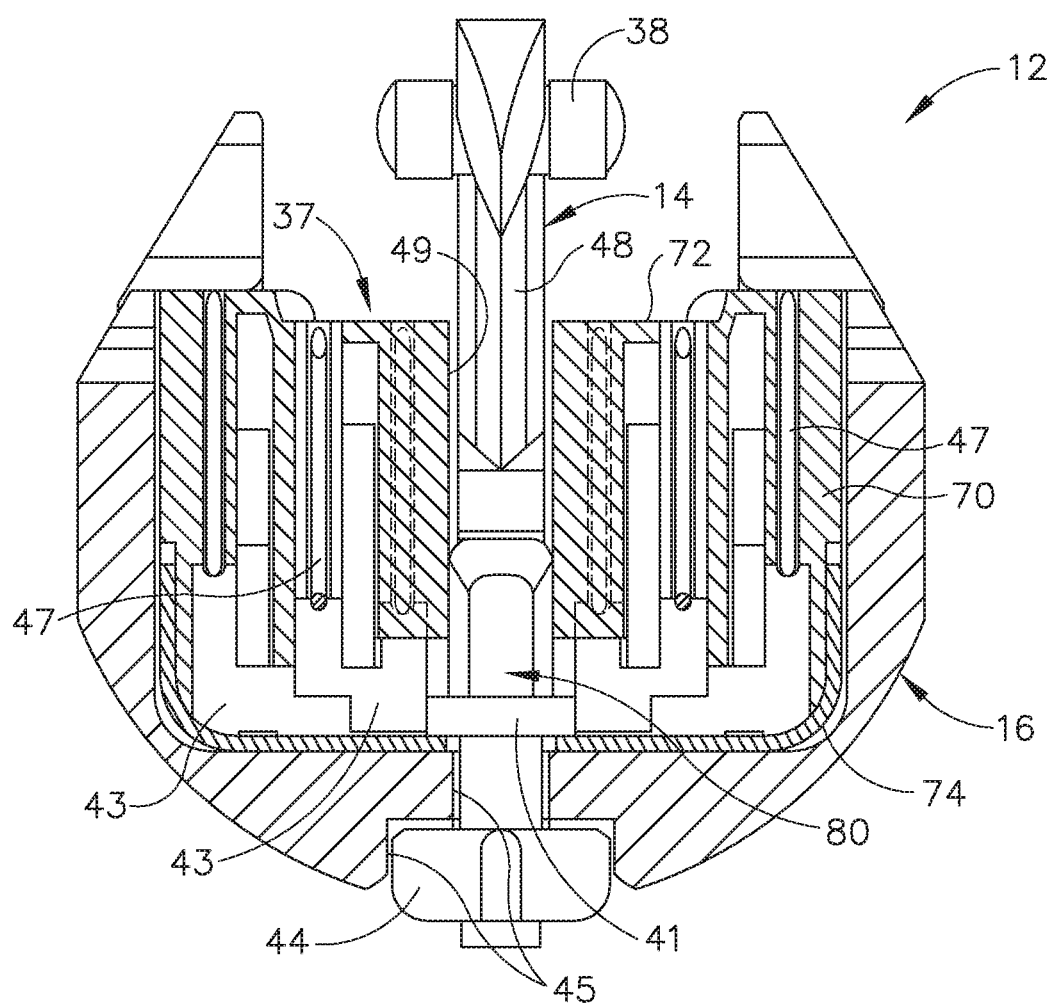
FIG. 5 depicts an end cross-sectional view of the end effector of FIG. 3, taken along line 5-5 of FIG. 3.
Figure 6:
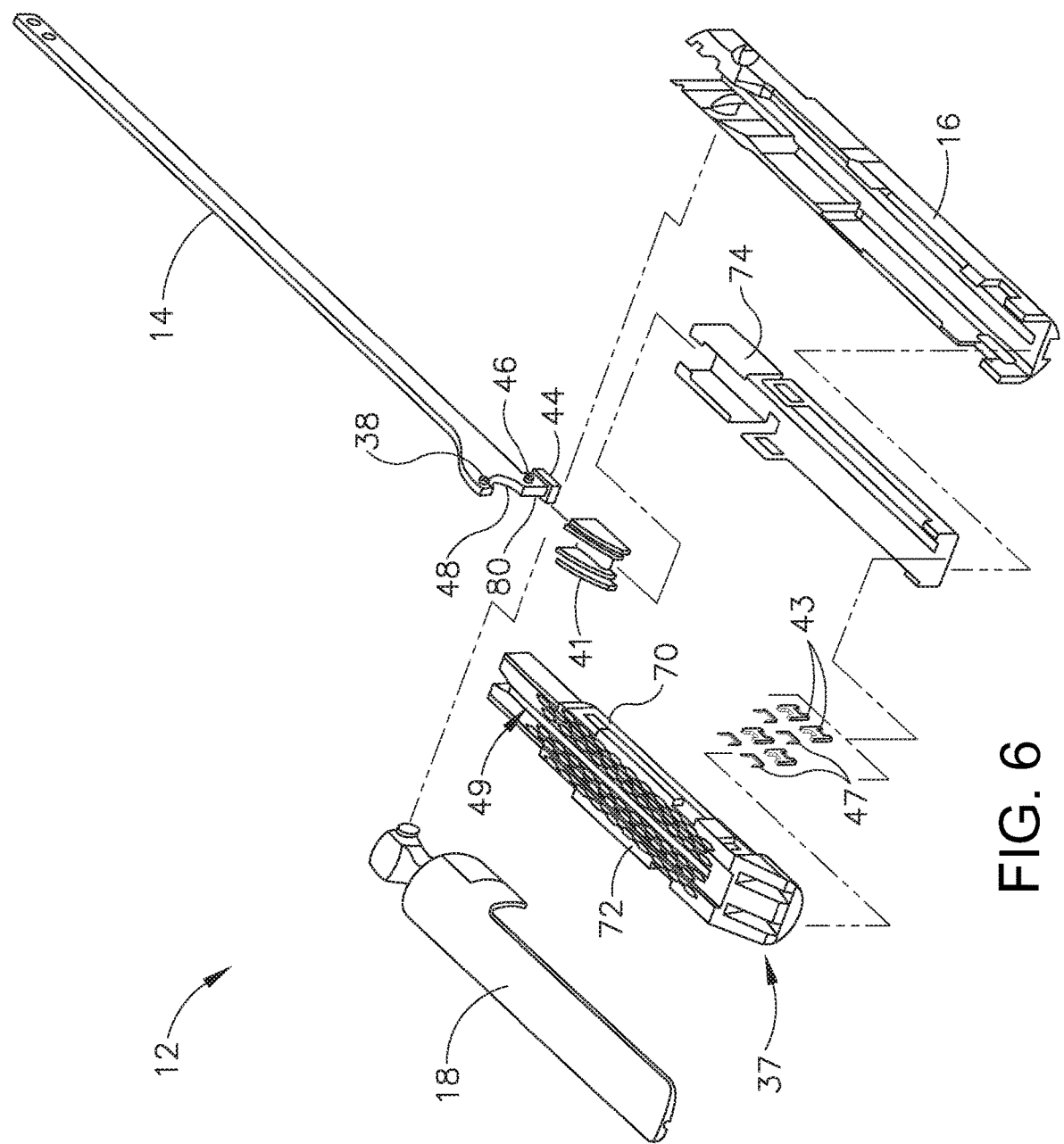
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
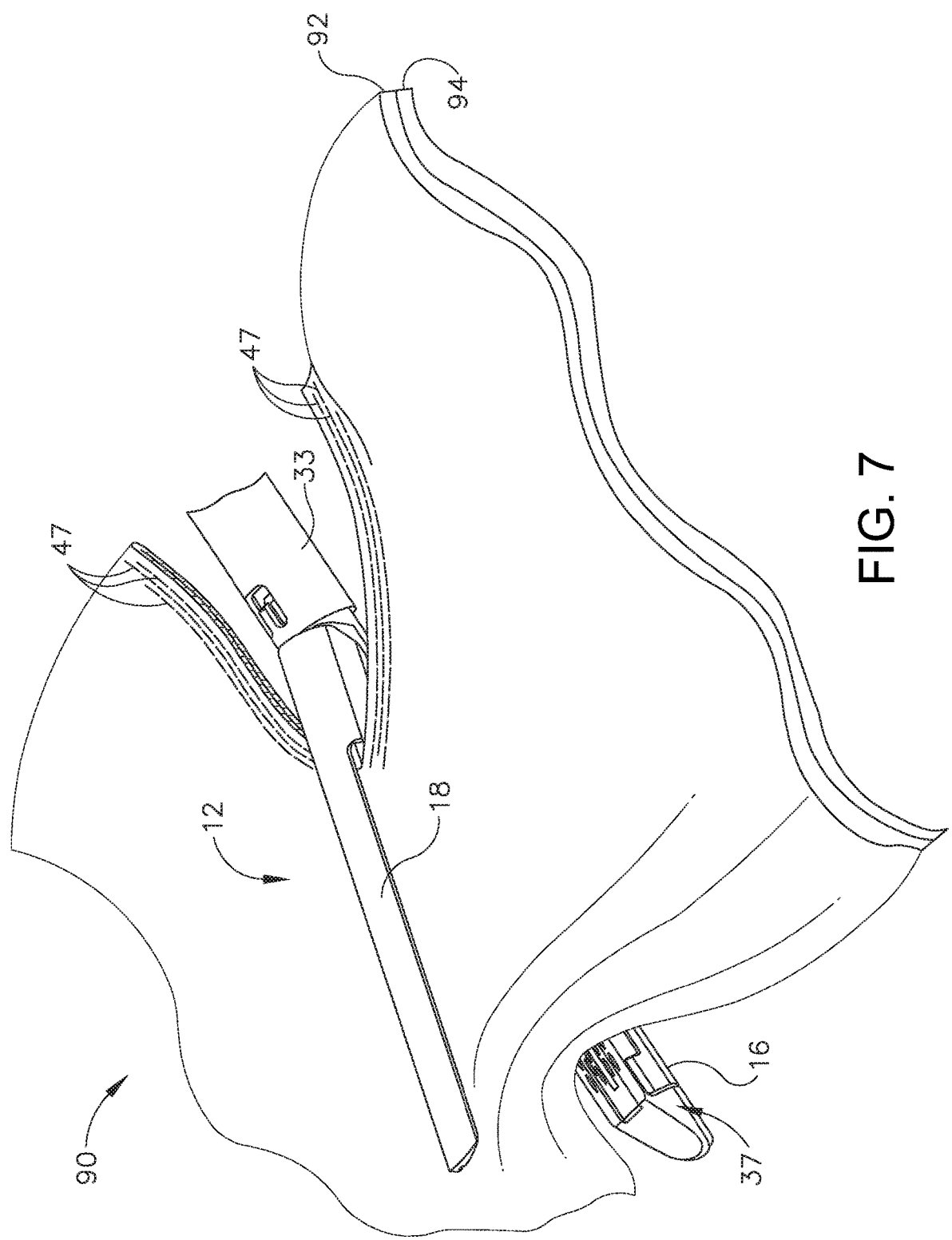
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47)

may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-in, and Gathering Feature In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
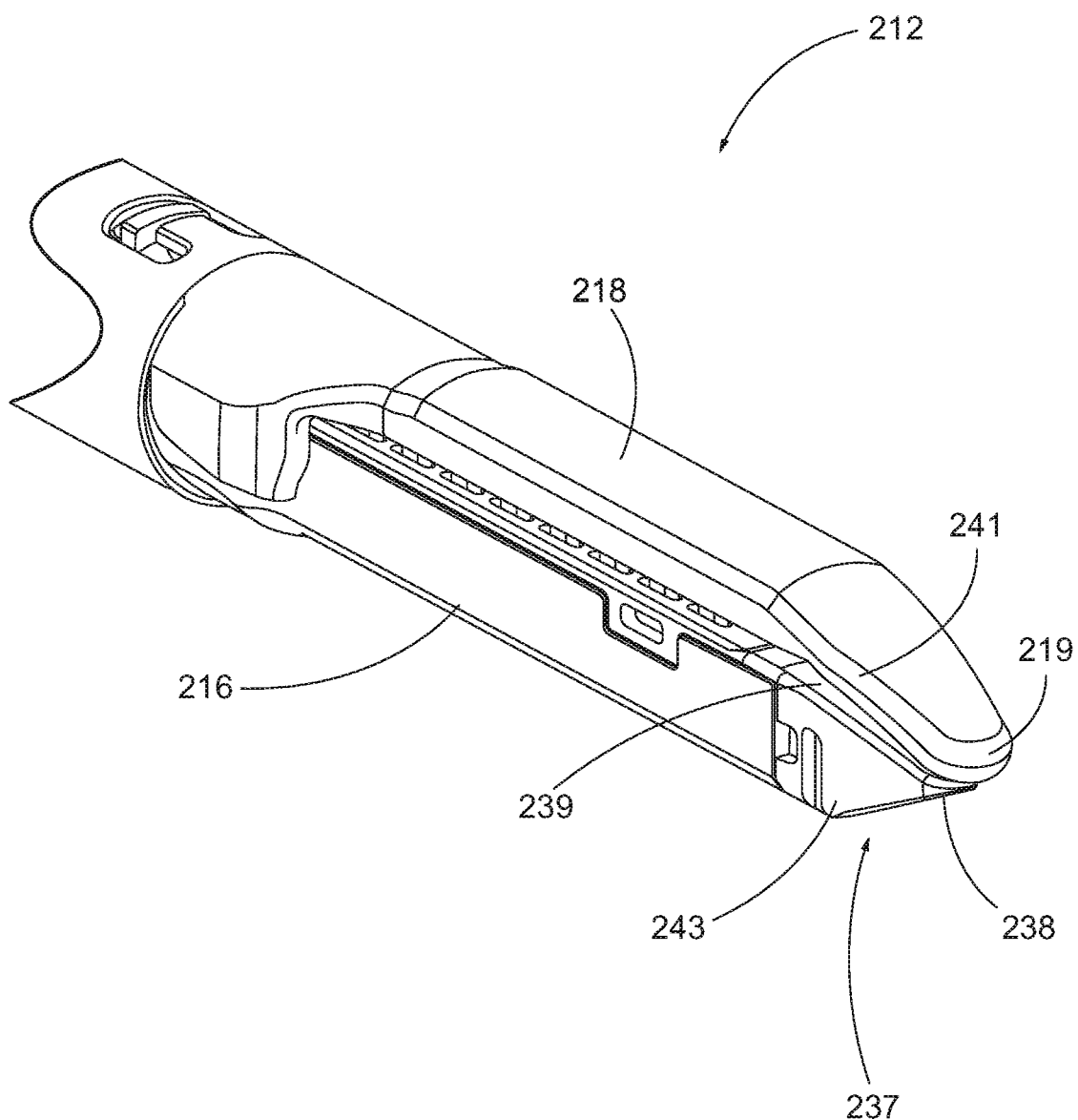
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
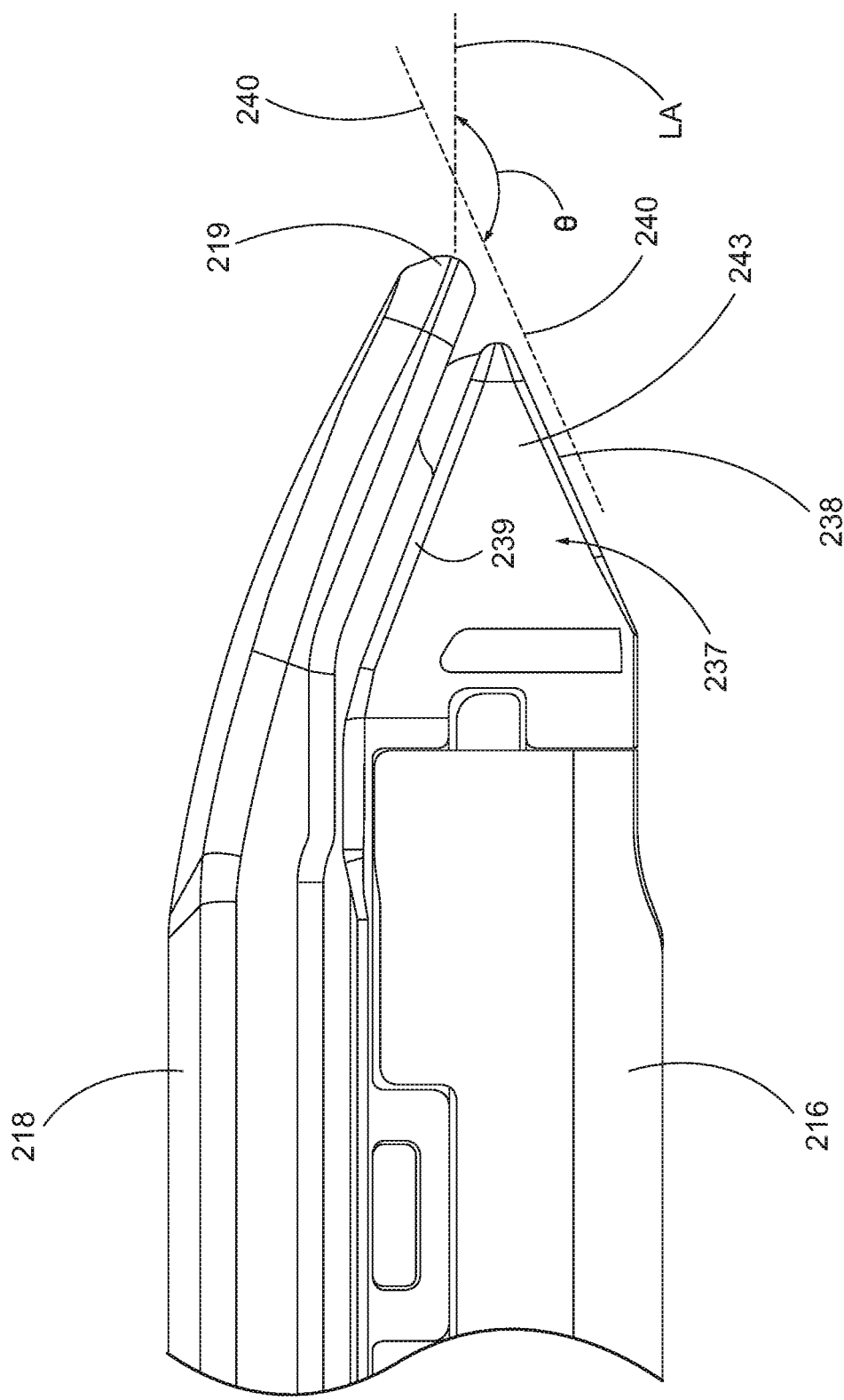
FIG. 9 depicts an enlarged, side view of the end effector of FIG. 8.
Figure 10:
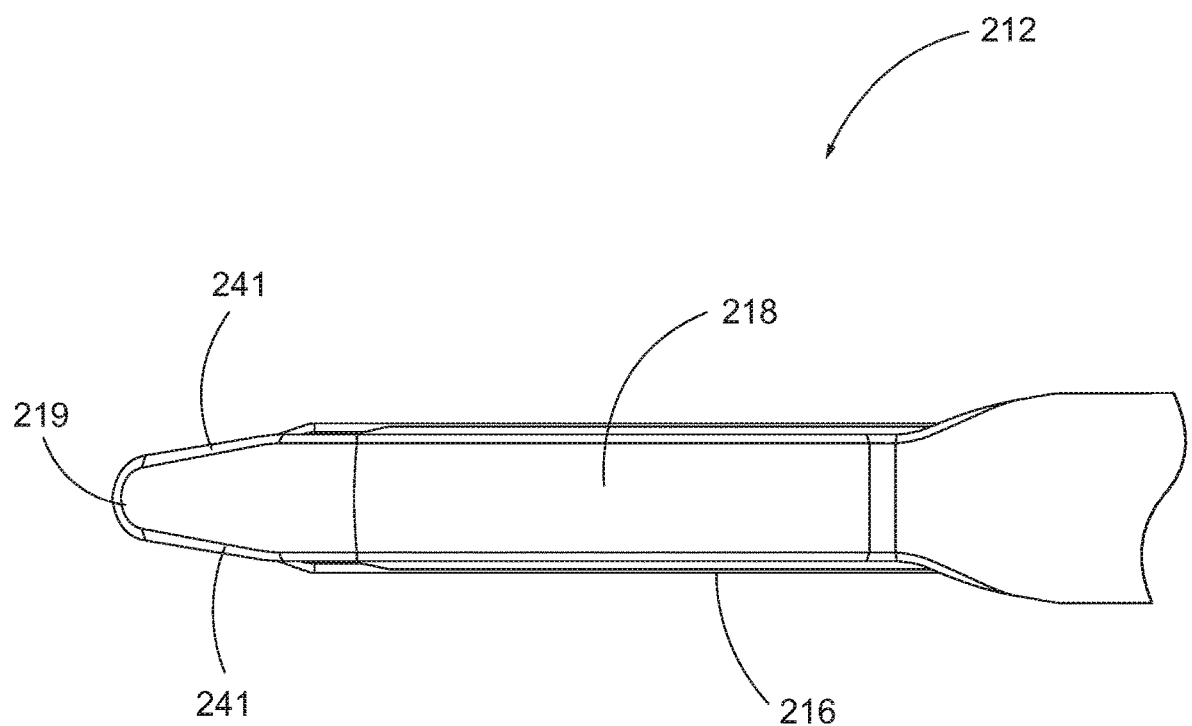
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. End Effectors with Bent or Angled Elastically Deformable Anvil Tips

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
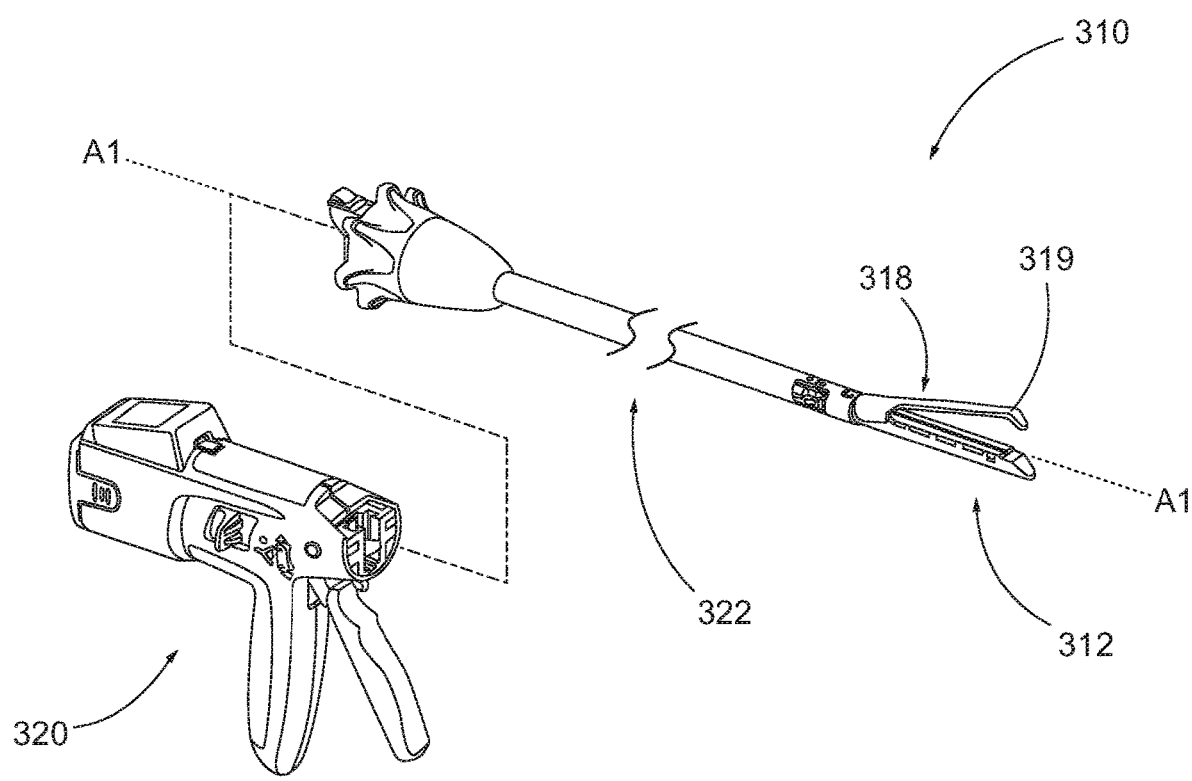
FIG. 11 depicts a perspective view of an exemplary surgical stapling instrument having an end effector with a bent or angled elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320).

Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. U.S. Pub. No. 2017/008623, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

IV. Exemplary Attachment for End Effector Deflectable Tip

In some instance where a surgical instrument incorporates a deflectable tip the same or similar to those described above, the deflectable tip can be a structure that is attached with the distal end of an end effector of the surgical instrument. In some cases, this attachment may be configured to create a permanent attachment between the deflectable tip and the end effector, but in other instances the attachment may be selective such that permanent attachment is not required. Regardless of the nature of the attachment, the deflectable tip is attached with the end effector such that it remains secured with the end effector during use of the instrument.

A. Mechanical Fastening

Figure 13:
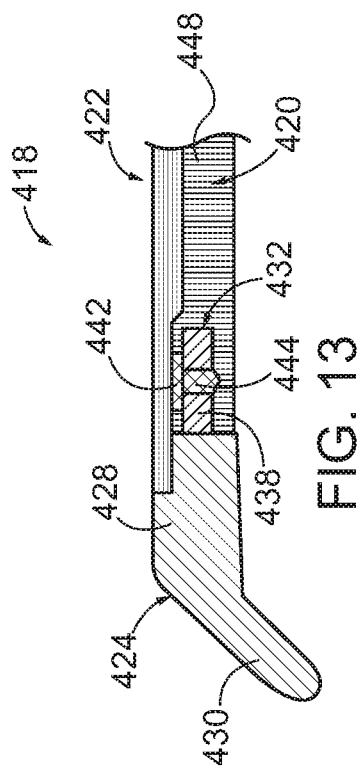
FIG. 13 depicts a side cross-sectional view of the end effector of FIG. 12.
Figure 14:
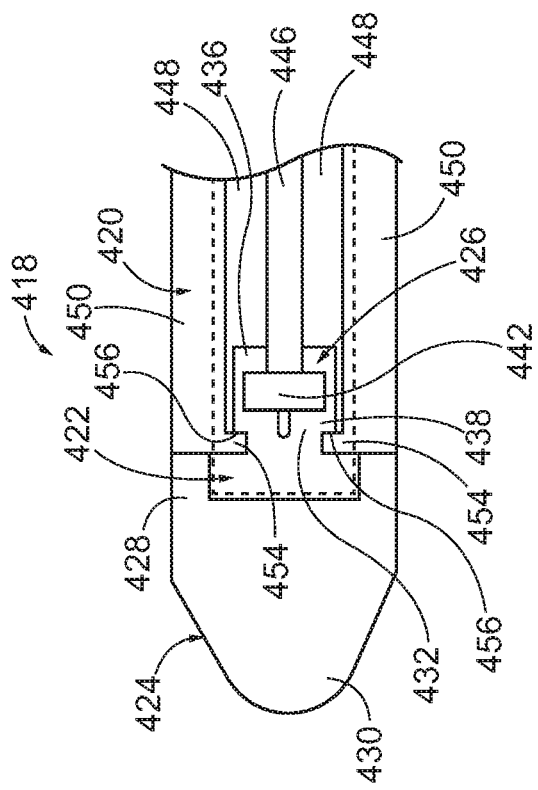
FIG. 14 depicts a top view of the end effector of FIG. 12, shown with a portion in phantom to reveal internal components.
Figure 12:
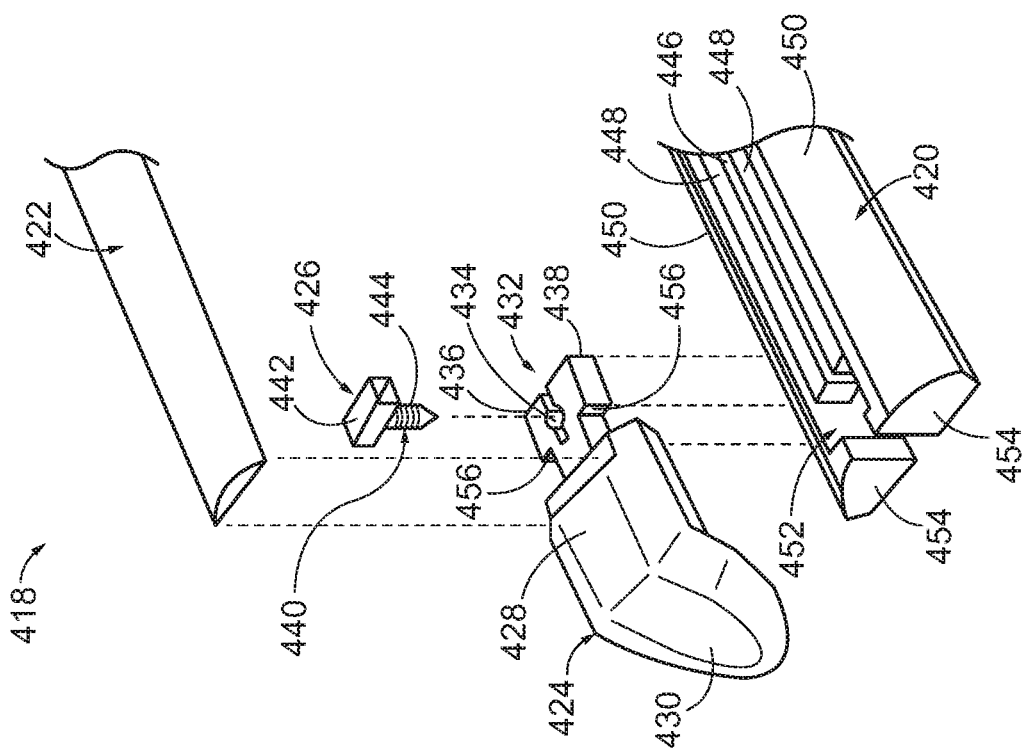
FIG. 12 depicts an exploded perspective view of an enlarged portion of an exemplary end effector having a deflectable tip.

FIGS. 12-14 depicts views of an enlarged portion of a jaw (418) of an end effector, which is configured for use with instruments (10, 310) and/or for robotic use as described above. Jaw (418), is positionable opposite to another jaw, such as jaw (16) or jaw (216) as described above in forming the end effector. Jaw (418) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (418) may be used with a variety of end effectors, at least some of which are described herein or incorporated by reference.

In the illustrated example, jaw (418) comprises a base (420), a cap (422), a placement tip (424), and a retention feature (426). Placement tip (424) is elastically deformable, and extends distally from the base (420) when assembled. As shown in the illustrated version, placement tip (424) is bent or angled such that a proximal portion (428) of placement tip (424) and a distal portion (430) define an angle that is less than 180 degrees. Still in other versions, placement tip (424) is not required to be bent or angled, and instead placement tip (424) is straight such that proximal portion (428) and distal portion (430) are co-planar and define an angle that is 180 degrees or thereabout. Still in other versions, placement tip (424) may be curved, wherein as placement tip (424) extends distally, placement tip (424) curves toward the opposing jaw. In view of the teachings herein, other shapes and ways to configure placement tip (424) will be apparent to those of ordinary skill in the art.

A connection member (432) extends proximally from proximal portion (428) of placement tip (424). Connection member (432) is configured with an opening (434) as well as first lateral projecting wing (436) and second lateral projecting wing (438). In the present example, opening (434) is located between first and second lateral projecting wings (436, 438). Furthermore, opening (434) is configured to receive retention feature (426) when attaching placement tip (424) with base (420). When retention feature (426) is inserted within opening (434), first and second lateral projecting wings (436, 438) deflect laterally away from opening (434). This deflection of first and second lateral projecting wings (436, 438) increases the contact or engagement between placement tip (424) and base (420), which aids in securing placement tip (424) with base (420).

As mentioned, retention feature (426) is configured to secure placement tip (424) with jaw (418), and in the present example with base (420) of jaw (418). Retention feature (426) is further configured to prevent removal of placement tip (424) from jaw (418). In the present example, retention feature (426) comprises gripping features (440) in the form of ribs or threads that are configured to bite into or engage the surface of first and second lateral projecting wings (436, 438) that defines opening (434). In this manner, retention feature (426) securely attaches with connection member (432), and as mentioned, imparts an outward force on first and second lateral projecting wings (436, 438) causing wings (436, 438) to deflect outward and engage with base (420). In view of the teachings herein, other ways to modify or configure retention member (426) to provide for secure attachment with placement tip (424) will be apparent to those of ordinary skill in the art.

As shown in FIG. 12, in the present version retention feature (426) comprises a fastener, such as a tack or similar fastener, having a body (442) and post (444) extending from body (442). Post (444) includes gripping features (440) described above. In the illustrated example of FIGS. 12-14, jaw (418) is configured such that retention feature (426) connects or attaches placement tip (424) with base (420) by locating retention feature (426) above placement tip (424) and advancing retention feature (426) downward such that post (444) extends through opening (434) of connection member (432). In this manner, retention feature (426) is insertable from the side of base (420) that faces away from or is farthest from the opposing jaw used with jaw (418) in forming the end effector.

Base (420) comprises central channel (446) defined between and by inner elongated portions (448). Base (420) further comprises outer elongated portions (450) that extend parallel to inner elongated portions (448). Although not required in all versions, elongated portions (448, 450) may be formed together as a unitary structure. At a distal end of base (420), a space (452) is defined between inner elongated portions (448 and outer elongated portions (450). Space (452) is configured with a complementary shape to connection member (432), such that connection member (432) is able to fit within space (452). In this manner, space (452) can also be considered a notch or cut-out configured to receive connection member (432). Base (420) further includes a bottom surface beneath space (452) such that connection member (432) cannot pass through space (452). As shown, outer elongated portions (450) each comprise distal flange (454). Distal flanges (454) are configured to abut or contact shoulder portions (456) of connection member (432) when connection member (432) is within space (452). In this manner, this interference fitting prevents placement tip (424) from distal separation from base (420).

Jaw (418) further comprises cap (422) as mentioned above. Cap (422) is configured to attach with base (420) and with part of proximal portion (428) of placement tip (426). Furthermore, cap (422) installs from above placement tip (424), retention feature (426), and base (420). In this manner, cap (422) covers retention feature (426) such that retention feature (426) is concealed within jaw (418). Furthermore, in the present example, an underside surface of cap (422) contacts body (442) of retention feature (426) to further secure retention feature (426) in place. As will be described below, cap (422) is not required in all versions, nor is it required in all versions that retention feature (426) is entirely concealed within jaw (418). In the present example, cap (422) is configured to permanently attach with base (420) and the part of placement tip (424) as shown. This permanent attachment of cap (422) is achieved by welding cap (422) in place, but can be permanently attached other ways like adhesives, mechanical fasteners, etc. In other versions, cap (422) is configured to securely but selectively connect with or attach with base (420) and the part of placement tip (424). In view of the teachings herein, other ways to configure cap (422) to connect with other components of jaw (418) to secure placement tip (424) with jaw (418) will be apparent to those of ordinary skill in the art in view of the teachings herein.

Figure 16:
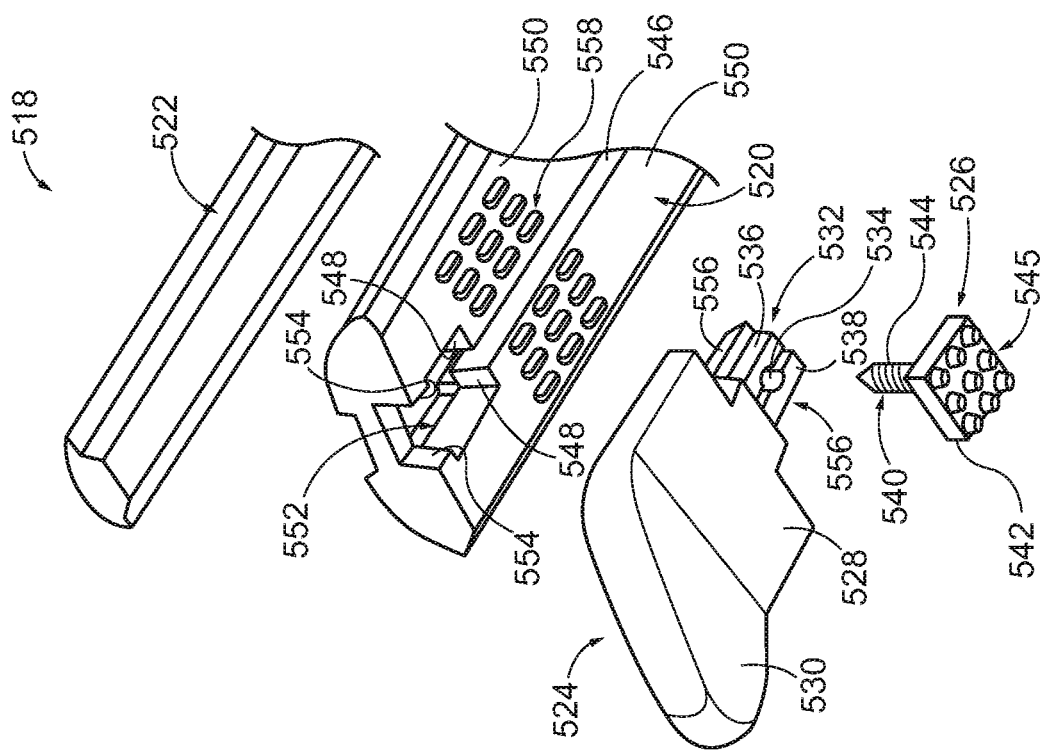
FIG. 16 depicts a perspective view of the end effector of FIG. 15.
Figure 15:
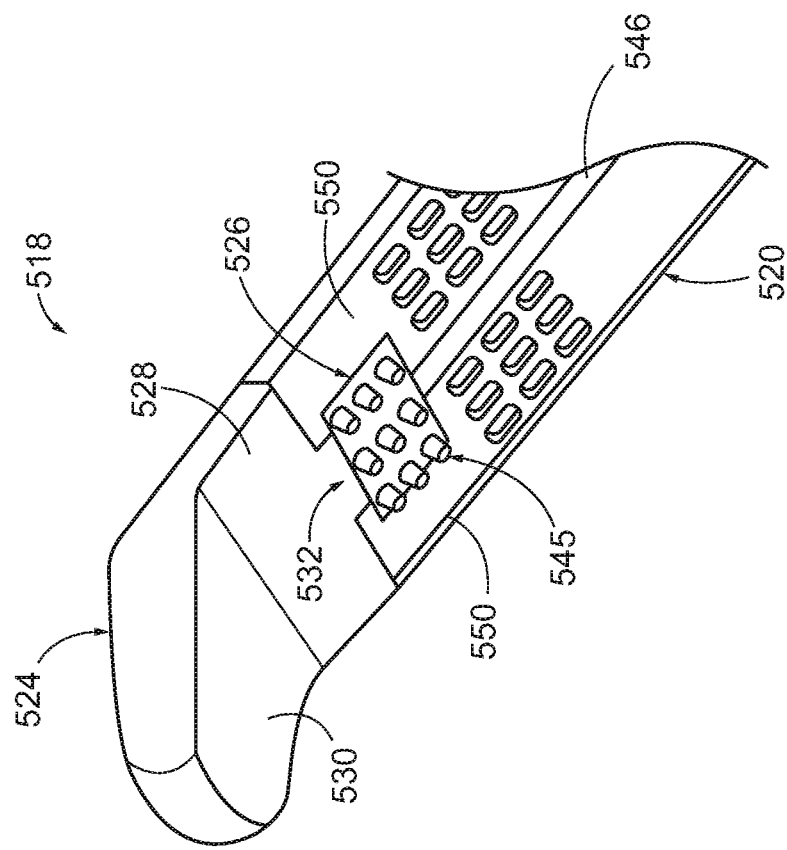
FIG. 15 depicts an exploded perspective view of an enlarged portion of an exemplary end effector having a deflectable tip.

FIGS. 15 and 16 depicts views of an enlarged portion of a jaw (518) of an end effector, which is configured for use with instruments (10, 310) and/or for robotic use as described above. Jaw (518), is positionable opposite to another jaw, such as jaw (16) or jaw (216) as described above in forming the end effector. Jaw (518) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (518) may be used with a variety of end effectors, at least some of which are described herein or incorporated by reference.

In the illustrated version, jaw (518) comprises a base (520), a cap (522), a placement tip (524), and a retention feature (526). Placement tip (524) is elastically deformable, and extends distally from the base (520) when assembled. As shown in the illustrated version, placement tip (524) is bent or angled such that a proximal portion (528) of placement tip (524) and a distal portion (530) define an angle that is less than 180 degrees. Still in other versions, placement tip (524) is not required to be bent or angled, and instead placement tip (524) is straight such that proximal portion (528) and distal portion (530) are co-planar and define an angle that is 180 degrees or thereabout. Still in other versions, placement tip (524) may be curved, wherein as placement tip (524) extends distally, placement tip (524) curves toward the opposing jaw. In view of the teachings herein, other shapes and ways to configure placement tip (524) will be apparent to those of ordinary skill in the art.

A connection member (532) extends proximally from proximal portion (528) of placement tip (524). Connection member (532) is configured with an opening (534) as well as first lateral projecting wing (536) and second lateral projecting wing (538). In the present example, opening (534) is located between first and second lateral projecting wings (536, 538). Furthermore, opening (534) is configured to receive retention feature (526) when attaching placement tip (524) with base (520). When retention feature (526) is inserted within opening (534), first and second lateral projecting wings (536, 538) deflect laterally away from opening (534). This deflection of first and second lateral projecting wings (536, 538) increases the contact or engagement between placement tip (524) and base (520), which aids in securing placement tip (524) with base (520).

As mentioned, retention feature (526) is configured to secure placement tip (524) with jaw (518), and in the present example with base (520) of jaw (518). Retention feature (526) is further configured to prevent removal of placement tip (524) from jaw (518). In the present example, retention feature (526) comprises gripping features (540) in the form of ribs or threads that are configured to bite into or engage the surface of first and second lateral projecting wings (536, 538) that defines opening (534). In this manner, retention feature (526) securely attaches with connection member (532), and as mentioned, imparts an outward force on first and second lateral projecting wings (536, 538) causing wings (536, 538) to deflect outward and engage with base (520). In view of the teachings herein, other ways to modify or configure retention member (526) to provide for secure attachment with placement tip (524) will be apparent to those of ordinary skill in the art.

As best shown in FIG. 16, in the present version retention feature (526) comprises a fastener, such as a tack or similar fastener, having a body (542) and post (544) extending from body (442). Post (444) includes gripping features (440) described above. Body (442) comprises gripping features (545), which are configured to assist in gripping tissue grasped between jaw (518) and the opposing jaw of the end effector using jaw (518). In the illustrated example of FIGS. 15 and 16, jaw (518) is configured such that retention feature (526) connects or attaches placement tip (524) with base (520) by locating retention feature (526) below placement tip (524) and advancing retention feature (526) upward such that post (544) extends through opening (534) of connection member (532). In this manner, retention feature (526) is insertable from the side of base (520) facing or closest to the opposing jaw used with jaw (518) in forming the end effector.

Base (520) comprises central channel (546) defined between and by inner elongated portions (548). Base (520) further comprises outer elongated portions (550) that extend parallel to inner elongated portions (548). Although not required in all versions, elongated portions (548, 550) may be formed together as a unitary structure. At a distal end of base (520), a space (552) is defined between inner elongated portions (548 and outer elongated portions (550). Space (552) is configured with a complementary shape to connection member (532), such that connection member (532) is able to fit within space (552). In this manner, space (552) can also be considered a notch or cut-out configured to receive connection member (532). Base (520) further includes a top surface above space (552) such that connection member (532) cannot pass through space (552). As shown, outer elongated portions (550) join at the distal end of base (520) and comprise distal flange (554). Distal flange (554) is configured to abut or contact shoulder portions (556) of connection member (532) when connection member (532) is within space (552). In this manner, this interference fitting prevents placement tip (524) from distal separation from base (520).

Jaw (518) further comprises cap (522) as mentioned above. Cap (522) is configured to attach with base (520), and in particular with an upper surface of base (520). As shown in FIG. 15, with jaw (518) assembled, the only portion of retention feature (526) that is exposed or revealed is the surface facing the opposing jaw that includes gripping features (545). While FIG. 16 illustrates cap (522) as part of jaw (518), in some other versions, cap (522) is omitted entirely. In the illustrated version of FIG. 16 where cap (522) is present, cap (522) is configured to permanently attach with base (520). This permanent attachment of cap (522) is achieved by welding cap (522) in place, but can be permanently attached other ways like adhesives, mechanical fasteners, etc. Still, in other versions, cap (522) is configured to securely but selectively connect with or attach with base (520). In view of the teachings herein, other ways to configure cap (522) to connect with other components of jaw (518) to secure placement tip (524) with jaw (518) will be apparent to those of ordinary skill in the art in view of the teachings herein.

In the above described versions of jaws (418, 518), each of jaw (418, 518) is configured as an anvil, where each base (420, 520) comprises a plurality of staple forming pockets on an underside surface. For instance, FIG. 16 illustrates staple forming pockets (558). With this configuration, the opposing jaw to jaws (418, 518) comprise a jaw that is configured to retain a stapling cartridge. By way of example, and not limitation, as mentioned above, jaws (16, 216) described above may be used in conjunction with either of jaws (418, 518) when configuring the end effector for use with surgical instruments (10, 310). In some other versions, jaws (418, 518) are not required to comprise an anvil, and instead may be configured or modified such that jaws (418, 518) may comprise a cartridge, with the opposing jaw configured with an anvil. In view of the teachings herein, other ways to configure jaws (418, 518) for use with an end effector for a surgical instrument (10, 310) will be apparent to those of ordinary skill in the art.

B. Surface Treatment and Features with Overmolding

While the above section describes and illustrates ways of attaching a deflectable placement tip with a jaw of an end effector using a retention feature such as a fastener or tack, other ways to attach a deflectable placement tip with a jaw of an end effector include overmolding the placement tip onto a part of the jaw of the end effector. With the description of the jaws that follow, surface treatments and/or features are added to the jaws to provide for improved overmolding attachment of the deformable or deflectable placement tip, and to prevent detachment and edge peeling.

Figure 17:
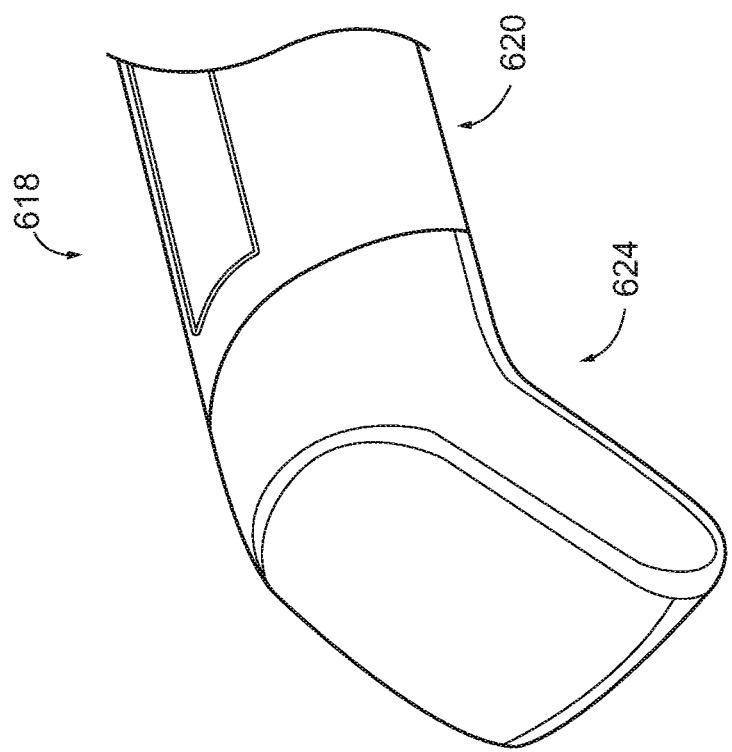
FIG. 17 depicts a perspective view of an enlarged portion of an exemplary end effector having a deflectable tip.

FIG. 17 depicts a perspective view of a portion of an exemplary jaw (618) of an end effector, which is configured for use with instruments (10, 310) and/or for robotic use as described above. Jaw (618), is positionable opposite to another jaw, such as jaw (16) or jaw (216) as described above in forming the end effector. Jaw (618) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (618) may be used with a variety of end effectors, at least some of which are described herein or incorporated by reference.

Figure 18:
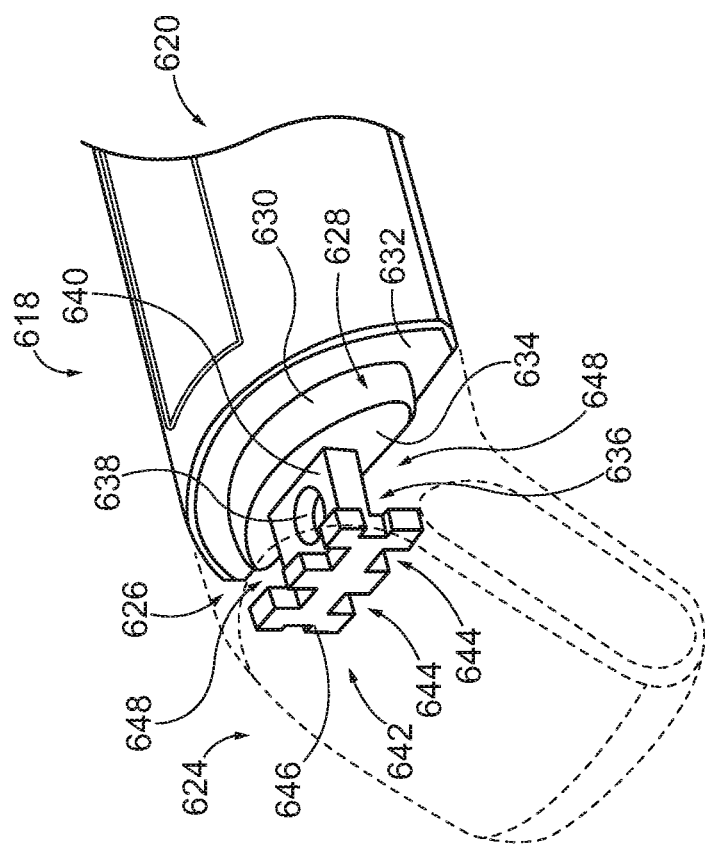
FIG. 18 depicts a perspective view of the end effector of FIG. 17, shown with the deflectable tip in phantom to show other components of the end effector.

Referring to FIGS. 17 and 18, jaw (618) comprises a body (620) and a placement tip (624). With respect to FIG. 18, placement tip (624) is shown in phantom to reveal further features of body (620) as will be described further below. In the present example, body (620) comprises an anvil that includes staple forming pockets and a channel for a cutting blade as described above. In other versions, body (620) is not required to be configured as the anvil, and instead the anvil may be the opposite jaw to jaw (620). In such other versions, body (620) can be configured to retain a staple cartridge as described above.

Returning now to the present illustrated example, body or anvil (620) comprises a distal portion (626). Distal portion (626) comprises connection features that are configured to improve the overmolding attachment of placement tip (624) with body (620). One such connection feature comprises a protrusion (628). Protrusion (628) has a similar shape with the majority of body (620), but is sized slightly smaller. Protrusion (628) extends distally from the remainder of body (620) and defines a bonding surface (630) that extends around the circumference of protrusion (628) and that is oriented orthogonally to a bonding surface (632) defined by body (620). Protrusion (628) further defines another bonding surface (634), which is generally orthogonal to bonding surface (630) and parallel with bonding surface (632).

Another connection feature of distal portion (626) is protrusion (636), which extends distally from protrusion (628). Protrusion (636) comprises a rectangular prism having a bore (638) extending therethrough. Bore (638) acts as a connection feature by providing space where material of the overmolded placement tip (624) can flow and bond to. Furthermore, protrusion (636) also defines another connection feature with a bonding surface (640) on the four sides of protrusion. Bonding surface (640) is oriented orthogonally to bonding surface (634) of protrusion (628).

Another connection feature of distal portion (626) is protrusion (642), which is at the distal end of distal portion (626). Protrusion (642) is oriented orthogonally relative to protrusion (636) from which it is attached. Protrusion (642) further comprises a plurality of notches (644) that act as additional connection features by providing space where material of the overmolded placement tip (624) can flow and bond to. In this manner, notches (644) provide increased surface area for material bonding during the overmolding process. In the illustrated version, but not required in all versions, protrusion (642) comprises six notches. Furthermore, each of the six notches are generally shaped the same, as square cut-outs. In some other versions, greater or fewer notches, and/or notches having other shapes or varying shapes can be used. In view of the teachings herein, other ways to configure protrusion (642) and notches (644) will be apparent to those of ordinary skill in the art. In addition to the bonding surfaces provided by notches (644), protrusion (642) further defines a bonding surface (646) on proximal and distal surfaces of protrusion (642). Bonding surface (646) is oriented orthogonally relative to bonding surface (640) of protrusion (636).

With the above described configuration of body (620) and in particular distal portion (626), improved overmolding is achieved by incorporating a plurality of connection features. Moreover, these connection features can have the form of a series of protrusions (628, 636, 642) where each protrusion extends distally from the preceding protrusion. Still yet, these protrusions (628, 636, 642) are configured to present alternating orthogonally oriented bonding surfaces (630, 640, 646). Another noteworthy connection feature of distal portion (626) comprises the relative sizes of protrusions (628, 636, 642). In particular, the middle protrusion, protrusion (636), has a smaller lateral dimension or width than the other protrusions (628, 642). With this configuration, distal portion (626) defines voids (648) on each side of protrusion (636) where material for overmolding placement tip (624) can flow. While a variety of connection features have been shown and described above, other ways to configure or modify distal portion (626) to define various connection features to improve overmolding will be apparent to those of ordinary skill in the art in view of the teachings herein. Furthermore, some such modifications can include using the various connection features presented independently from one another or in other combinations other than those depicted in FIGS. 17 and 18.

Sometimes with surgical instruments such as instruments (10, 310) that use end effectors as described herein for surgical cutting and stapling, lubricants are applied to the anvil portions of the end effector jaws. Added lubricant can help promote better sliding of the staples along the forming pockets as well as better sliding of the blade or knife through the anvil longitudinal channel. In some instances, it may be desirable to remove lubricant from distal portion (626) where the overmolding occurs, or to prevent lubricant from being applied to distal portion (626) in the first instance. Such removal or prevention of lubrication can provide for improved overmolding attachment of placement tip (624) with body or anvil (620).

In one example, lubricant is applied to body (620), including distal portion (626), and then before overmolding, the lubricant is removed from distal portion (626) by an etching application. Etching distal portion (626) can provided additional benefit in roughening the surface of distal portion (626) to promote better bonding of the material used for overmolding with distal portion (626). In another example, distal portion (626) is masked or covered prior to lubricating body (620) such that distal portion (626) remains free of lubricant. In this way, better overmolding success can be achieved where distal portion (626) remains free of lubricant. Still in another example, combinations of masking and etching can be used. In view of the teachings herein, other ways to lubricate portions of jaw (618) in a targeted manner such that improved overmolding can be achieved will be apparent to those of ordinary skill in the art.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprises (a) a body, (b) a shaft extending from the body, wherein the shaft defines a first longitudinal axis, and (c) an end effector in communication with the shaft. The end effector is operable to compress, staple, and cut tissue. The end effector comprises: (i) a first jaw, (ii) a second jaw opposing the first jaw, wherein at least one of the jaws is movable relative to the other jaw between an open position and a closed position, (iii) a placement tip that is elastically deformable, wherein the placement tip extends distally from the first jaw, and (iv) a retention feature configured to secure the placement tip with the first jaw, wherein the retention feature is further configured to prevent removal of the placement tip when the retention feature is installed.

Example 2

The apparatus of Example 1, wherein the retention feature connects a proximal portion of the placement tip with the first jaw.

Example 3

The apparatus of any one or more of Examples 1 through 2, wherein the retention feature comprises a fastener.

Example 4

The apparatus of Example 3, wherein the proximal portion of the placement tip comprises a connection member, wherein the connection member comprises an opening configured to receive the fastener.

Example 5

The apparatus of Example 4, wherein the first jaw comprises a void space having a complementary shape to the connection member of the placement tip.

Example 6

The apparatus of any one or more of Examples 4 through 5, wherein the connection member further comprises an extension member, wherein the opening of the connection member extends through at least a portion of the extension member.

Example 7

The apparatus of Example 6, wherein the extension member comprises a first lateral projecting wing and a second lateral projecting wing, wherein insertion of the fastener within the opening of the connection member deflects the first and second projecting wings of the extension member outward from a second longitudinal axis defined by the placement tip.

Example 8

The apparatus of Example 7, wherein deflection of the first and second projecting wings increases a contact pressure between the first and second projecting wings and the first jaw.

Example 9

The apparatus of any one or more of Examples 1 through 8, wherein the first jaw comprises an underside surface facing the second jaw, wherein the retention feature is configured to be installed from a top surface of the first jaw that is opposite the underside surface of the first jaw.

Example 10

The apparatus of any one or more of Examples 1 through 9, wherein the first jaw comprises a base and a cap configured to selectively attach with the base.

Example 11

The apparatus of any one or more of Examples 1 through 8 and 10, wherein the first jaw comprises an underside surface facing the second jaw, wherein the retention feature is configured to be installed from the underside surface of the first jaw.

Example 12

The apparatus of any one or more of Examples 1 through 11, wherein the retention feature comprises gripping features.

Example 13

The apparatus of Example 12, wherein the gripping features extend toward the second jaw.

Example 14

The apparatus of any one or more of Examples 1 through 13, wherein the first jaw comprises an anvil.

Example 15

The apparatus of any one or more of Examples 1 through 14, wherein the retention feature is substantially concealed within the first jaw.

Example 16

An apparatus comprises: (a) a body, (b) a shaft extending from the body, wherein the shaft defines a first longitudinal axis; and (c) an end effector in communication with the shaft. The end effector is operable to compress, staple, and cut tissue. The end effector comprises: (i) a placement tip that is elastically deformable, (ii) a first jaw, wherein the first jaw comprises a surface feature at a distal end of the first jaw, wherein the surface feature is configured for overmolding attachment of the placement tip with the first jaw such that the placement tip extends distally from the first jaw, wherein the surface feature of the first jaw is further configured to prevent detachment of the overmolded placement tip, and (ii) a second jaw opposing the first jaw, wherein at least one of the jaws is movable relative to the other jaw between an open position and a closed position.

Example 17

The apparatus of Example 16, wherein the surface feature of the first jaw is at least substantially surrounded by the overmolded placement tip.

Example 18

The apparatus of any one or more of Examples 16 through 17, wherein the surface feature is further configured to prevent edge peeling of the overmolded placement tip.

Example 19

The apparatus of any one or more of Examples 16 through 18, wherein the surface feature comprises: (A) a first portion extending longitudinally relative to the first jaw, wherein the first portion comprises a bore extending therethrough, and (B) a second portion connected to the first portion, wherein the second portion extends orthogonally relative to the first portion, wherein the second portion comprises a plurality of notches.

Example 20

A method of attaching a deflectable placement tip to an end effector of a surgical instrument, wherein the end effector comprises a first jaw having a surface feature at a distal end, and a second jaw opposing the first jaw, wherein at least one of the jaws is movable relative to the other jaw between an open position and a closed position, wherein the method comprises: (a) lubricating the first jaw, (b) preparing the surface feature of the first jaw for overmolding attachment of the placement tip, wherein preparing the surface feature comprises a select one of etching the surface feature to remove any lubricant from the surface feature, masking the surface feature prior to lubricating the first jaw to prevent lubricant from contacting the surface feature, and combinations thereof; and (c) overmolding the placement tip to the distal end of the first jaw, wherein the placement tip contacts and substantially surrounds the surface feature of the first jaw.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed Feb. 17, 2017, issued as U.S. Pat. No. D833,010 on Nov. 6, 2018, the disclosure of which is incorporated by reference herein. Various suitable ways in which the teachings herein may be combined with the teachings of U.S. patent application Ser. No. 29/594,335, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,573, filed Feb. 17, 2017, issued as U.S. Pat. No. 10,828,031 on Nov. 10, 2020, entitled "Surgical Stapler with Elastically Deformable Tip," the disclosure of which is incorporated by reference herein. Various suitable ways in which the teachings herein may be combined with the teachings of U.S. patent application Ser. No. 15/435,573, issued as U.S. Pat. No. 10,828,031 on Nov. 10, 2020 will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed Feb. 17, 2017, issued as U.S. Pat. No. 10,729,434 on Aug. 4, 2020, the disclosure of which is incorporated by reference herein. Various suitable ways in which the teachings herein may be combined with the teachings of U.S. patent application Ser. No. 15/435,607, issued on U.S. Pat. No. 10,729,434 on Aug. 4, 2020, will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed Feb. 17, 2017, issued as U.S. Pat. No. 10,806,451 on Oct. 20, 2020, the disclosure of which is incorporated by reference herein. Various suitable ways in which the teachings herein may be combined with the teachings of U.S. patent application Ser. No. 15/435,618, issued as U.S. Pat. No. 10,806,451 on Oct. 20, 2020, will be apparent to those of ordinary skill in the art.

It should also be understood that the teachings herein may be readily combined with various teachings in U.S. patent application Ser. No. 29/594,340, entitled "End Effector for a Surgical Stapler," filed Feb. 17, 2017, issued as U.S. Pat. No. D863,199 on Dec. 18, 2018, the disclosure of which is incorporated by reference herein. Various suitable ways in which the teachings herein may be combined with the teachings of U.S. patent application Ser. No. 29/594,340, issued as U.S. Pat. No. D863,199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, issued as U.S. Pat. No. 10,758,231 on Sep. 1, 2020, will be apparent to those of ordinary skill in the art.

It should also be understood that the teachings herein may be readily combined with various teachings in U.S. patent application Ser. No. 16/035,856, entitled "Surgical Stapling End Effector Component with Tip Having Varying Bend Angle," filed on Jul. 16, 2018, published as U.S. Pub. No. 2018/0325514 on Nov. 15, 2018, the disclosure of which is incorporated by reference herein. Various suitable ways in which the teachings herein may be combined with the teachings of U.S. patent application Ser. No. 16/035,856, published as U.S. Pub. No. 2018/0325514 on Nov. 15, 2018, will be apparent to those of ordinary skill in the art.

It should also be understood that the teachings herein may be readily combined with various teachings in U.S. patent application Ser. No. 16/035,890, entitled "Surgical Stapling End Effector Jaw with Tip Deflecting Toward Other Jaw," filed on Jul. 16, 2018, published as U.S. Pub. No. 2018/0325515 on Nov. 15, 2018, the disclosure of which is incorporated by reference herein. Various suitable ways in which the teachings herein may be combined with the teachings of U.S. patent application Ser. No. 16/035,890, published as U.S. Pub. No. 2018/0325515 on Nov. 15, 2018, will be apparent to those of ordinary skill in the art.

It should also be understood that the teachings herein may be readily combined with various teachings in U.S. patent application Ser. No. 16/035,865 "Method of Surgical Stapling with End Effector Component Having a Curved Tip," filed on Jul. 16, 2018, published as U.S. Pub. No. 2018/0325516 on Nov. 15, 2018, the disclosure of which is incorporated by reference herein. Various suitable ways in which the teachings herein may be combined with the teachings of U.S. patent application Ser. No. 16/035,865, published as U.S. Pub. No. 2018/0325516 on Nov. 15, 2018, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
(a) a body;

(b) a shaft extending from the body, wherein the shaft defines a first longitudinal axis; and
(c) an end effector in communication with the shaft, wherein the end effector is operable to compress, staple, and cut tissue, wherein the end effector comprises:
  (i) a first jaw extending longitudinally, wherein a distal end of the jaw includes a void space that opens orthogonally and is at least partially closed distally,
  (ii) a second jaw opposing the first jaw, wherein at least one of the jaws is movable relative to the other jaw between an open position and a closed position,
  (iii) a placement tip that is elastically deformable, wherein the placement tip extends distally from the first jaw and includes a connection member configured to be received orthogonally within the void space to inhibit the placement tip from separating distally from the distal end of the first jaw, and
  (iv) a retention feature configured to secure the connection member within the opening and thereby secure the placement tip with the first jaw, wherein the retention feature is further configured to prevent removal of the placement tip when the retention feature is installed,
wherein a proximal portion of the placement tip comprises the connection member, wherein the connection member comprises an opening configured to receive the retention feature.

2. The apparatus of claim 1, wherein the retention feature connects a proximal portion of the placement tip with the first jaw.

3. The apparatus of claim 1, wherein the retention feature comprises a fastener, wherein the opening of the connection member is configured to receive the fastener.

4. The apparatus of claim 1, wherein the void space has a complementary shape to the connection member of the placement tip.

5. The apparatus of claim 1, wherein the connection member further comprises an extension member, wherein the opening of the connection member extends through at least a portion of the extension member.

6. The apparatus of claim 5, wherein the extension member comprises a first lateral projecting wing and a second lateral projecting wing, wherein insertion of the fastener within the opening of the connection member deflects the first and second lateral projecting wings of the extension member outward from a second longitudinal axis defined by the placement tip.

7. The apparatus of claim 6, wherein deflection of the first and second lateral projecting wings increases a contact pressure between the first and second projecting wings and the first jaw.

8. The apparatus of claim 1, wherein the first jaw comprises an underside surface facing the second jaw, wherein the retention feature is configured to be installed from a top surface of the first jaw that is opposite the underside surface of the first jaw.

9. The apparatus of claim 8, wherein the first jaw comprises a base and a cap configured to selectively attach with the base.

10. The apparatus of claim 1, wherein the first jaw comprises an underside surface facing the second jaw, wherein the retention feature is configured to be installed from the underside surface of the first jaw.

11. The apparatus of claim 1, wherein the retention feature comprises gripping features.

12. The apparatus of claim 11, wherein the gripping features extend toward the second jaw.

13. The apparatus of claim 1, wherein the first jaw comprises an anvil.

14. The apparatus of claim 1, wherein the retention feature is substantially concealed within the first jaw.

15. The apparatus of claim 1, wherein the void space is partially open distally.

16. An apparatus, comprising:
(a) a body;
(b) a shaft extending from the body, wherein the shaft defines a first longitudinal axis; and
(c) an end effector in communication with the shaft, wherein the end effector is operable to compress, staple, and cut tissue, wherein the end effector comprises:
  (i) a placement tip that is elastically deformable,
  (ii) a first jaw, wherein the first jaw comprises a surface feature at a distal end of the first jaw, wherein the surface feature includes a first portion extending parallel to a longitudinal axis of the first jaw and a second portion extending orthogonally relative to the first portion, wherein the surface feature is configured for overmolding attachment of the placement tip with the first jaw such that the placement tip extends distally from the first jaw, wherein the surface feature of the first jaw is further configured to prevent detachment of the overmolded placement tip, and
  (ii) a second jaw opposing the first jaw, wherein at least one of the jaws is movable relative to the other jaw between an open position and a closed position.

17. The apparatus of claim 16, wherein the surface feature of the first jaw is at least substantially surrounded by the overmolded placement tip.

18. The apparatus of claim 16, wherein the surface feature is further configured to prevent edge peeling of the overmolded placement tip.

19. The apparatus of claim 16, wherein the first portion comprises a bore extending therethrough, and wherein the second portion comprises a plurality of notches.

20. An apparatus, comprising:
(a) a body;
(b) a shaft extending from the body, wherein the shaft defines a longitudinal axis; and
(c) an end effector in communication with the shaft, wherein the end effector is operable to compress, staple, and cut tissue, wherein the end effector comprises:
  (i) a first jaw,
  (ii) a second jaw opposing the first jaw, wherein at least one of the jaws is movable relative to the other jaw between an open position and a closed position,
  (iii) a placement tip that is elastically deformable, wherein the placement tip extends distally from the first jaw, and
  (iv) a retention feature configured to secure the placement tip with the first jaw, wherein the retention feature is further configured to prevent removal of the placement tip when the retention feature is coupled with the placement tip and the first jaw, wherein the retention feature includes a gripping feature configured to assist in gripping tissue between the first and second jaws.

* * * * *